United States Patent [19]

Kantor et al.

[11] Patent Number: 4,649,143
[45] Date of Patent: Mar. 10, 1987

[54] METHODS AND COMPOSITIONS FOR TREATING PROTOZOAL INFECTIONS WITH A NOVEL ANTIBIOTIC

[75] Inventors: Sidney Kantor, Cranbury; Robert L. Kennett, Jr., Lambertville, both of N.J.

[73] Assignee: American Cyanamid Company, Stamford, Conn.

[21] Appl. No.: 593,152

[22] Filed: Mar. 26, 1984

[51] Int. Cl.$^4$ ............................................. A61K 31/44
[52] U.S. Cl. ..................................................... 514/279
[58] Field of Search ......................................... 514/279

[56] References Cited

U.S. PATENT DOCUMENTS 4,277,478  7/1981  Zahner et al. ................... 424/258

Primary Examiner—Frederick E. Waddell
Attorney, Agent, or Firm—Alice C. Brennan

[57] ABSTRACT

The present invention relates to methods and compositions for the control of protozoal infections, especially coccidial ones, in warm-blooded animals, such as meat-producing animals, i.e., poultry, by administering to the animals a protozoacidally-effective amount of a new antibiotic designated LL-D42067$\beta$, NRRL 15734. This novel antibiotic is produced via a controlled conditioned microbiological fermentation using a new strain of *Actinomadura madurae* subspecies *simaoensis* or mutants thereof.

8 Claims, 4 Drawing Figures

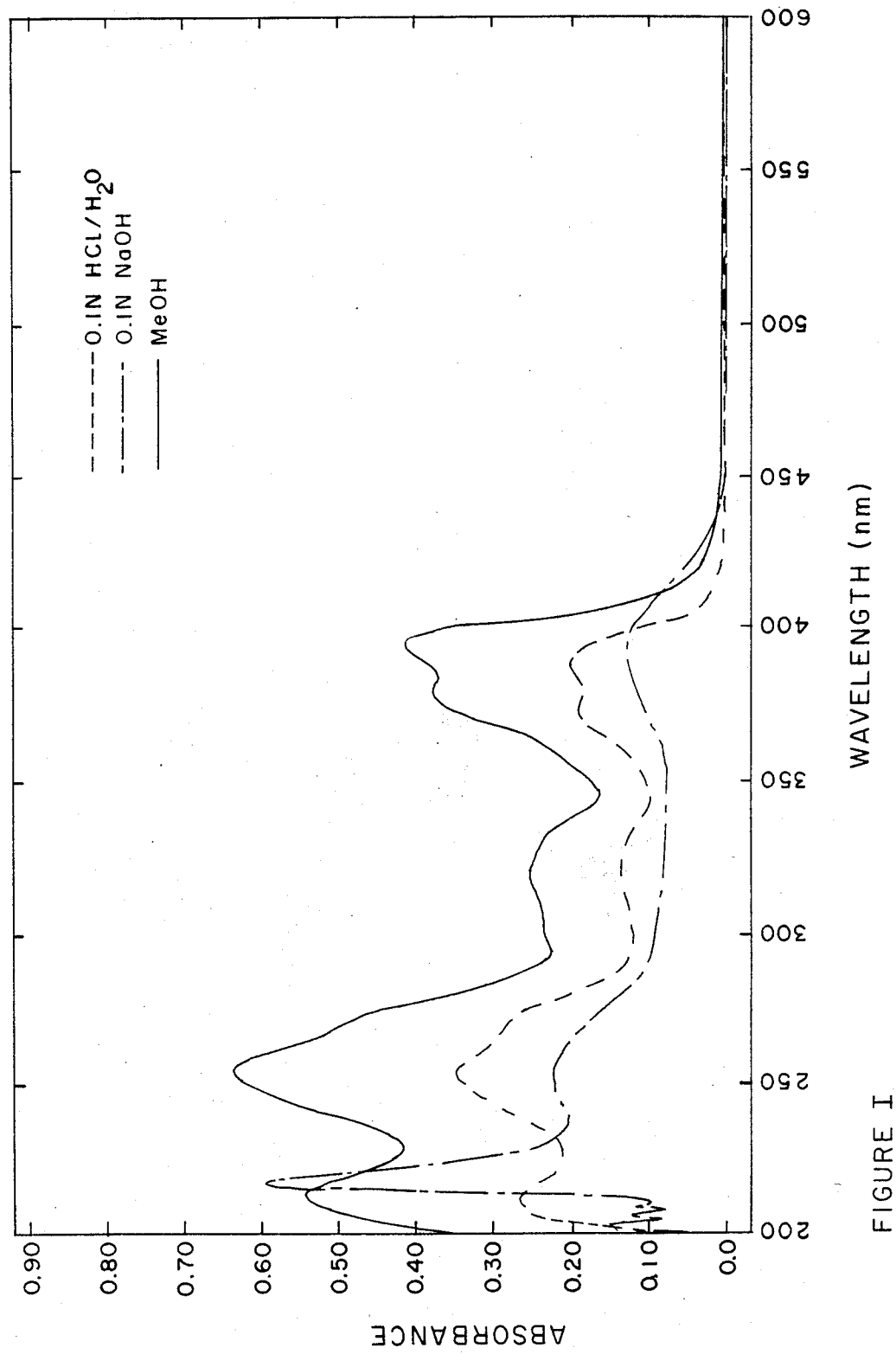
FIGURE I

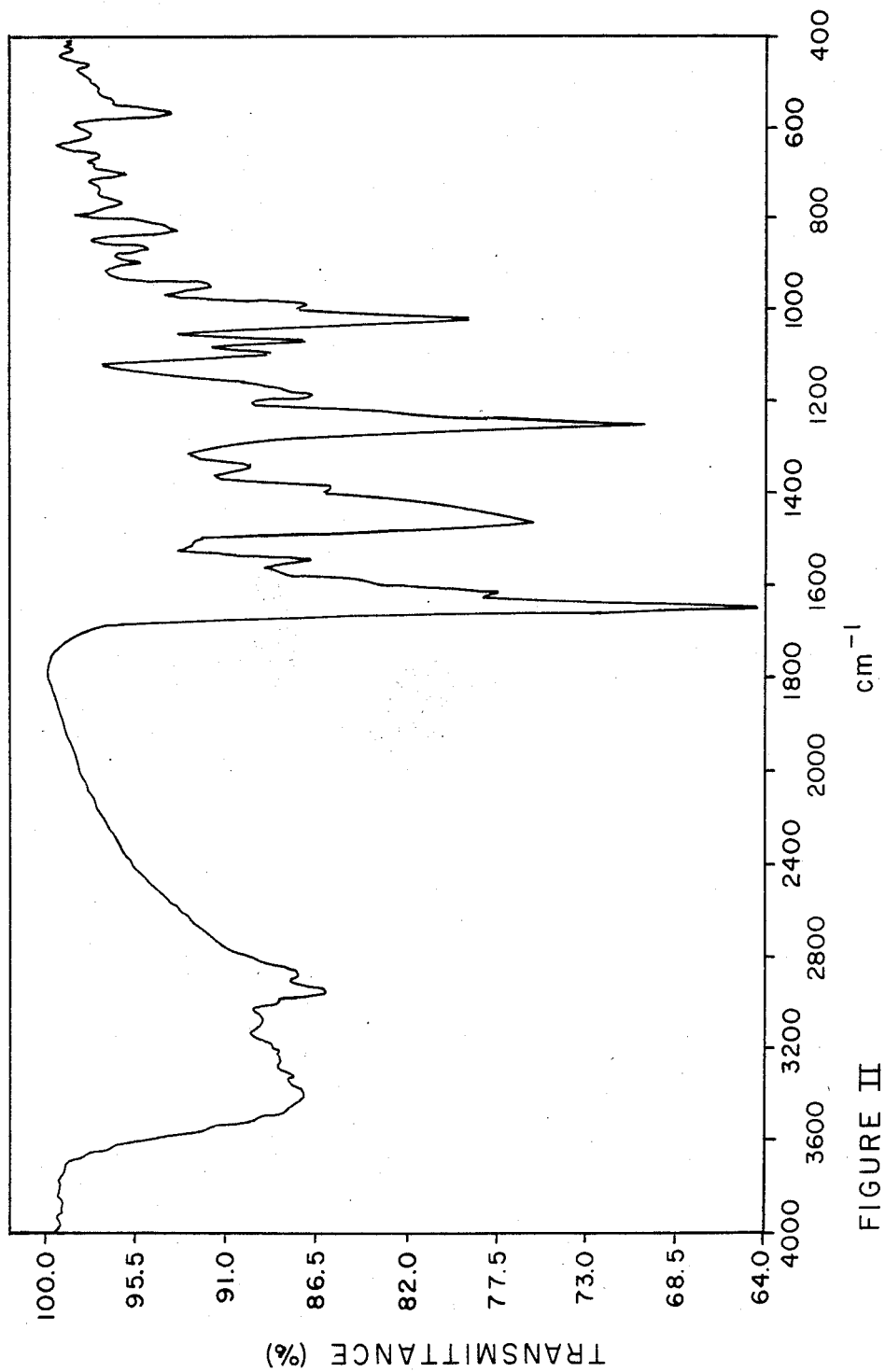
FIGURE II

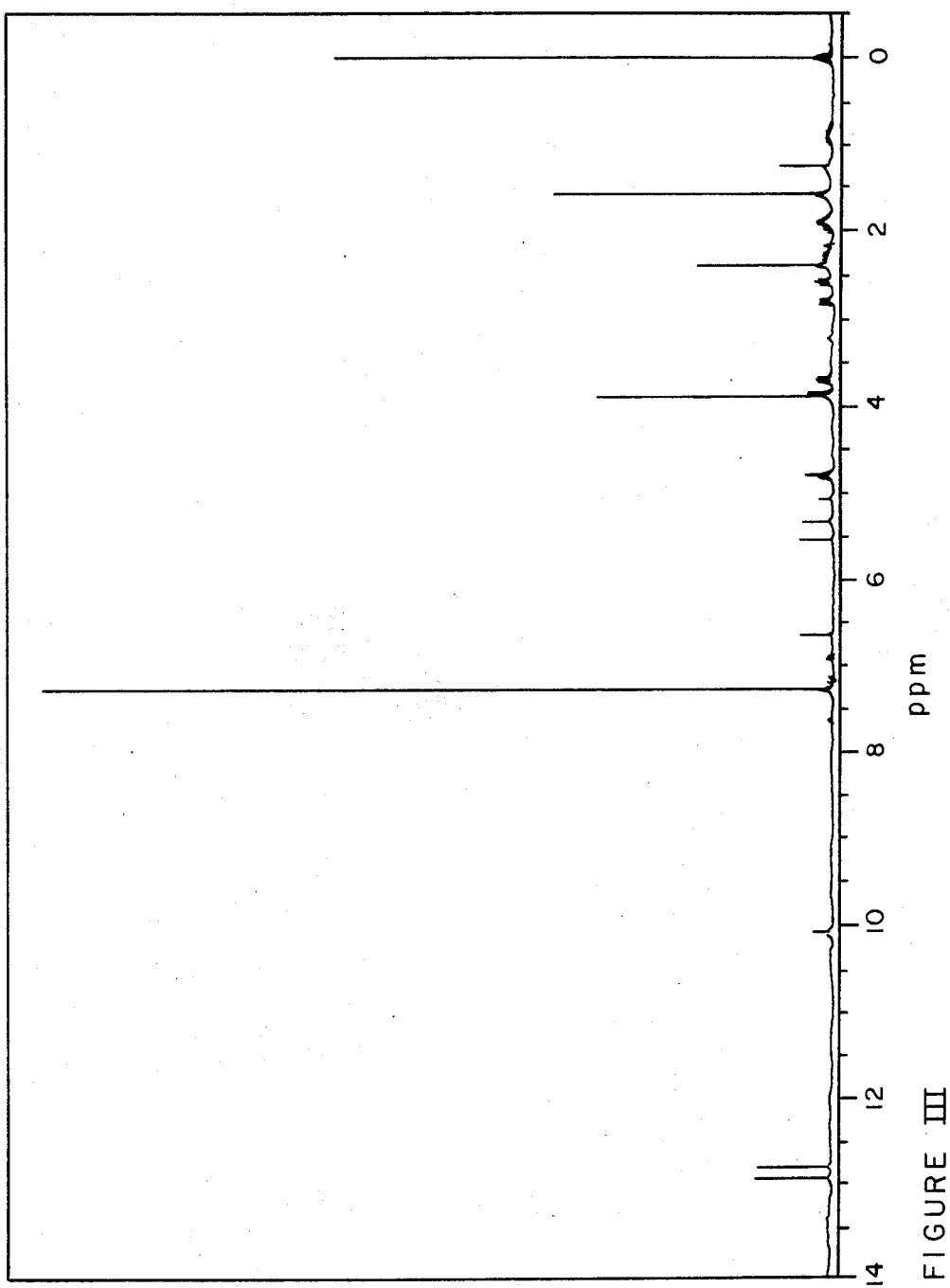

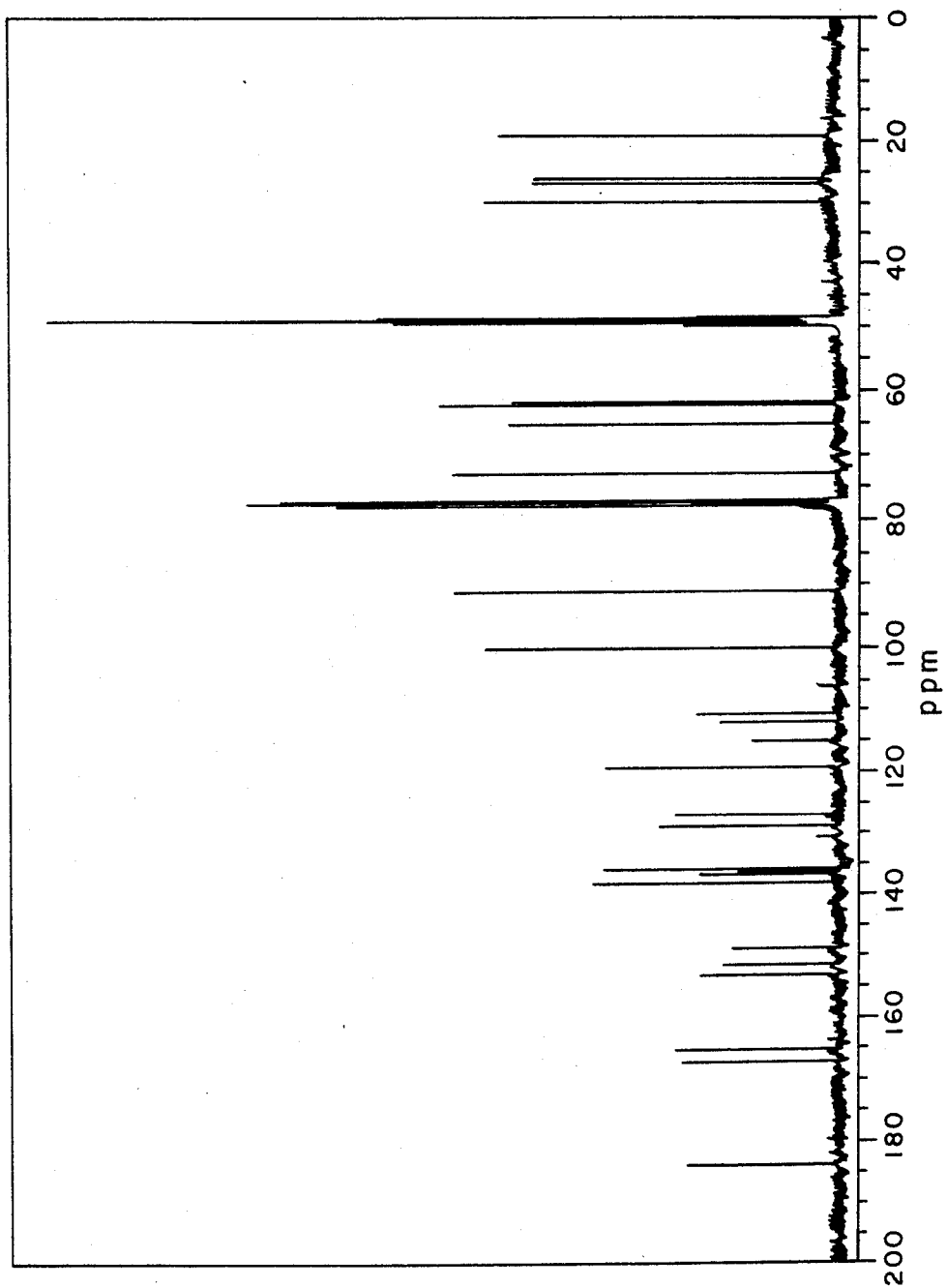

METHODS AND COMPOSITIONS FOR TREATING PROTOZOAL INFECTIONS WITH A NOVEL ANTIBIOTIC

BACKGROUND OF THE INVENTION

The present invention relates to methods and compositions for preventing, treating, or controlling protozoal infections in warm-blooded animals by administering thereto an effective amount of the antibiotic LL-D42067β.

Coccidiosis is one of the most important of the protozoan parasitic diseses which plague the meat-producing industry. It is responsible for significantly greater losses to the poultry industry than from any other protozoan disease and is likewise responsible for substantial economic loss among a wide variety of farm, companion, and game animals.

This disease is caused by protozoan parasites which infect the host animals causing them to lose weight, reduce their feed efficiency; and, in many instances, die. In poultry, these protozoan parasites are generally of the genus Eimeria; six species of which have been shown to be primary causative agents for the disease in poultry. These six species are: *Eimeria tenella, Eimeria necatrix, Eimeria mivati, Eimeria maxima, Eimeria brunetti, and Eimeria acervulina.*

Although coccidiosis has been recognized, for many years, as one of the most important diseases confronting the meat-producing industry, nevertheless, heretofore no entirely satisfactory method of control of the disease has been provided.

Anticoccidial treatments which have met with some acceptance by the poultry industry are the compounds described in the E. Waletzky et al., U.S. Pat. No. Re. 26,833, reissued Mar. 24, 1970; and A. S. Tomcufcik, U.S. Pat. No. 3,769,432, issued Oct. 30, 1973, and the W. D. Celmer et al., U.S. Pat. No. 4,148,882, issued Apr. 10, 1979. The drugs described in the patents are useful for the treatment of coccidial infections in poultry; however, new, more effective treatments are still required if the industry is to successfully control the disease that challenges meat production throughout the world.

SUMMARY OF THE INVENTION

It is, therefore, an object of this invention to provide a novel method for the control of protozoan infections in warm-blooded animals, particularly meat-producing animals such as poultry, swine, cattle, rabbits, and sheep.

It is also an object of this invention to provide novel compositions effective for the control of protozoan infections in meat-producing animals.

The present invention relates to novel methods and antibiotic compositions effective for controlling, treating, minimizing, preventing, ameliorating, or curing protozoal infections in farm, companion, and game animals, particularly in meat-producing animals such as poultry, cattle, sheep, swine, and rabbits, and companion animals such as rabbits, dogs, and cats.

The antibiotic which is useful in the methods and compositions of this invention is LL-D42067β, NRRL 15734. This antibiotic and method for the preparation thereof are described in the U.S. Pat. No. 4,578,468 of Guy Thomas Carter, Donald Bruce Borders, Joseph Jacob Goodman, and David Paul Labeda which issued on Mar. 26, 1986 and which is incorporated herein by reference thereto. This antibiotic, designated LL-D42067β, NRRL 15734, has the following structural formula:

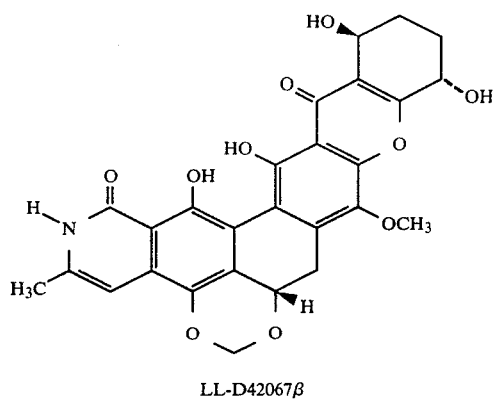

LL-D42067β

DESCRIPTION OF DRAWINGS

FIG. I: Characteristic ultraviolet absorption spectra of compound designated LL-D42067β, NRRL 5734.

FIG. II: Characteristic infrared absorption spectrum of compound designated LL-D42067β, NRRL 15734.

FIG. III: Characteristic proton nuclear magnetic resonance spectrum of compound designated LL-D42067β, NRRL 15734, in CD Cl$_3$ solution.

FIG. IV: Characteristic carbon-13 nuclear magnetic resonance spectrum of compound designated LL-D42067β, NRRL 15734, in CD$_3$ OD/CDCl$_3$ solution.

DETAILED DESCRIPTION OF THE INVENTION

It has been discovered that the above-mentioned antibiotic is especially effective for controlling coccidiosis caused by Eimeria species in meat-producing animals, particularly in poultry such as chickens, turkeys, ducks, geese, quail, and pheasants, and in cattle, sheep, swine, and rabbits.

It is also anticipated that the antibiotic compositions of this invention will prove to be effective for controlling malaria, toxoplasmosis, and sarcosporidiosis in warm-blooded animals since the causative agents for such diseases are protozoan infections and are biologically related to Eimeria.

In practice, the present invention involves the method of preventing, controlling, or treating protozoal infections, such as coccidiosis, in warm-blooded animals by administering thereto, a prophylactically, pharmaceutically, or therapeutically effective amount of the antibiotic compound designated LL-D42067β, NRRL 15734, or a pharmaceutically and pharmacologically acceptable salt thereof.

Although administration of the compound for coccidiosis will generally be most practical in or with the feed or in the drinking water, the above-said compound, or a pharmaceutically and pharmacologically acceptable salt thereof, may also be administered to individual hosts in the form of tablets, drenches, gels, capsules, or the like, or by injection in the form of a paste, gel, pellet, or solution. These latter methods of administration are, of course, less practical for the treatment of large groups of animals, but they are quite practical for use on a small scale or on an individual basis.

When the antibiotic LL-D42067β is used as a prophylactic or therapeutic treatment for coccidiosis in poultry, generally about 0.1 ppm to 10.0 ppm, and preferably, 0.5 ppm to 3.0 ppm of the antibiotic LL-D42067β, administered in the diet or drinking water of the poultry, is effective for preventing, controlling, or inhibiting coccidiosis in said animals.

As previously indicated, the antibiotic LL-D42067β, or a pharmaceutically and pharmacologically acceptable salt thereof, may also be employed as a prophylactic, pharmaceutical, or therapeutic treatment for the control, prevention, or inhibition of protozoal infections in other warm-blooded animals such as cattle, sheep, and swine. Generally, about 1.0 ppm to 100 ppm, and preferably 5 ppm to 50 ppm, of the antibiotic is effective for controlling protozoal infections, such as coccidiosis, in these larger animals.

Medicated poultry feeds useful in the method of the present invention are usually prepared by thoroughly admixing about 0.00001% by weight to about 0.0005% by weight of the antibiotic LL-D42067β with a nutritionally balanced poultry feed, as for example, the chick feed described in the examples hereinafter.

Medicated cattle, sheep, or swine feed can be prepared in the same manner as described above for the poultry feed excepting that 0.0001% by weight to 0.01% by weight of the antibiotic is admixed with the cattle, sheep, or swine feed.

When using the compound of the invention for the prevention or control of coccidiosis, the active anticoccidial agent is generally first prepared as an animal feed premix. The premix usually contains a relatively high percentage of the anticoccidial agent and is generally blended with the animal's feed just prior to administration. If desired, the feed premix may also be applied as a top dressing for the animal's daily ration.

Feed premixes or concentrates, useful in the practice of the present invention, may be prepared by admixing about 0.1% to 5.0% by weight of the above-identified antibiotic, or a pharmaceutically and pharmacologically acceptable salt thereof, with about 99.9% to 95% by weight of a suitable carrier or diluent. Carriers suitable for use to make up the feed supplement compositions include the following: alfalfa meal, soybean meal, cottonseed oil meal, linseed oil meal, sodium chloride, calcium carbonate, calcium sulfate, cornmeal, cane molasses, urea, bone meal, corn-cob meal, rice hull meal, and the like. The carrier promotes an essentially uniform distribution of the active ingredient in the finished feed into which the supplement is blended. It thus performs an important function by ensuring proper distribution of the active ingredient, i.e., about 0.1 ppm to 100 ppm thereof, throughout the feed. This is equivalent to 0.00001% to 0.01% by weight of the active ingredient in the finished feed. In practice, usually one or more pounds of premix is added per ton of feed to obtain the desired level of antibiotic in the finished feed.

If the supplement or premix is used as a top dressing for feed, it likewise helps to ensure uniformity of distribution of the active material across the top of the dressed feed.

Since the compound of this invention and its pharmaceutically and pharmacologically acceptable salts are relatively insoluble in water, it is generally desirable, when administering the compound in the animal's drinking water, to dissolve the active compound in an organic solvent such as methanol, ethanol, acetone, DMSO, oleic acid, linoleic acid, propylene glycol, or the like, and admix with the solution a small amount of surfactant and/or dispersing agent to assure solution and/or dispersion of the active ingredient in the animal's drinking water.

Advantageously, where the treatment of a small number of the larger meat-producing animals is required to control a protozoan infection therein, the antibiotic LL-D42067β or a pharmaceutically or pharmacologically acceptable salt thereof may be orally administered, on a daily basis, to the host animal in the form of a medicated gel.

The medicated gel may be prepared by admixing a medicated gellant phase with an aqueous buffer phase under reduced pressure 25–50 mm Hg at ambient temperature 20° C.–60° C. The gellant is prepared by dissolving or dispersing about 0.004% to about 4.5% by weight based on the final formulation of the antibiotic LL-D42067β or a pharmaceutically or pharmacologically acceptable salt thereof, in 14% to 31% by weight of propylene glycol based on the final formulation and about 15% to 50% by weight of the gellant at 60° C. to 80° C. Alternatively, the gellant phase may be prepared completely at ambient temperature as hereinafter described.

The gellant phase may be prepared by slurrying 0.004% by weight to about 4.5% b weight of the antibiotic LL-D42067β or a pharmaceutically or pharmacologically acceptable salt thereof, with the gellant 15% to 50%, and preferably 15% to 35% by weight of formulation in propylene glycol 14% to 30% by weight for 15 minutes to one hour under reduced pressure 25–50 mm Hg at room temperature. The gellant selected is a nonionic surfactant of structure α-hydro-Ω-hydroxypoly(oxyethylene)poly(oxypropylene)poly(oxyethylene) block copolymer, average molecular weight 12,500; mp 56° C.; Brookfield viscosity of 3,100 at 77° C.; surface tension of a 0.1% aqueous solution: 40.6 dynes/cm (measured with a du Nouy tensiometer).

An aqueous buffer solution may then be prepared by dissolving 1.5% by weight of citric acid and 1.0% by weight of trisodium citrate in about 3% by weight to about 25% by weight and preferably 6% to 12% by weight of final formulation in deionized or distilled water used in amounts of from about 15% by weight to about 50% by weight and preferably 35% to 45% by weight of formulation. This buffered solution provides a pH range at which long term chemical stability of the components of the gel formulation is achieved, i.e., pH 3–3.5.

Optional components which may be incorporated into the above solution at this stage are:

a. Benzyl alcohol added in amounts of from about 0.5% by weight to about 1.5% by weight and preferably 1.5% by weight of formulation as an antimicrobial preservative;

b. the yellow dye C.I. Acid yellow No. 23; ("tartrazine;" F.D. and C yellow No. 5; 4,5-dihydro-5-oxo-1-(4-sulfophenyl)-4-[(sulfophenyl)azo]-1H-pyrazole-3-carboxylic acid trisodium salt) used as coloring agent in amounts of from about 0.01% by weight to about 0.03% by weight and preferably 0.01% by weight of formulation;

c. an antifoaming agent comprising a mixture of dimethylpolysiloxanes of structure:

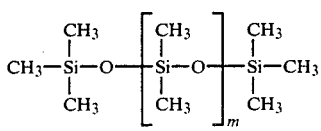

and silica gel, wherein the calculated average value of m is 200–350, the mixture is a water-white viscous oil-like liquid; d=0.965–0.970; $n_D^{25}$ about 1.404; viscosity about 60,000 centistrokes (and said antifoaming agent is described in U.S. Pat. No. 2,441,098) used in amounts of from 0.001–0.02% by weight and preferably 0.02% by weight of formulation.

The medicated gel is prepared by simply mixing either of the above-gellant phases and the aqueous solution from one-half to two hours under reduced pressure of from 10–100 mm Hg and preferably 25–50 mm Hg, at ambient temperatures of from 20° C. to 60° C. without the requirements of either additional heating or cooling. This procedure gives an air-free gel which is suitable for administering exact dosages of anticoccidial by volume. When careful control of dosage of active ingredients to be administered by volume is not necessary, and when the presence of air in the gel is acceptable in the final formulation, the preparation may be carried out at pressures up to and including atmospheric pressure.

By the above method, a typical gel of the invention may be prepared by dissolving 4.5 g of the antibiotic LL-D42067β, 1.5 g citric acid monohydrate, 1.0 g sodium citrate dihydrate, 1.5 g of benzyl alcohol, and 0.01 g of the yellow dye C.I. Acid yellow No. 23 in 42 g of water. Next, a solution of the above gellant 28 g in propylene glycol 21.99 g is prepared by mixing at 60° C. Then the solutions are mixed together under 25–50 mm Hg until a homogeneous mixture is obtained at 20° C. to 60° C. without additional heating or cooling. The gel formed has a gelation temperature range of from −15° C. to −18° C.; viscosity of the gel is 0.51×10+6; and the water gellant ratio is 1.5/1.0.

When 6.3 grams of this medicated gel are orally administered to a 200 pound (90.8 kg) fattening steer on a daily basis, said steer receives approximately 3 mg/kg of body weight/day of the protozoacidially-effective antibiotic LL-D42067β.

In practice, generally about 0.03 mg/kg/day to about 3.0 mg/kg/day is effective for controlling protozoan infections in cattle, sheep, and swine. For smaller companion animals, rates as low as 0.003 mg/kg of body weight/day may be employed.

The structure of LL-D42067β, shown above, has been elucidated by x-ray crystallography, and the relative stereochemistry of this compound is shown below.

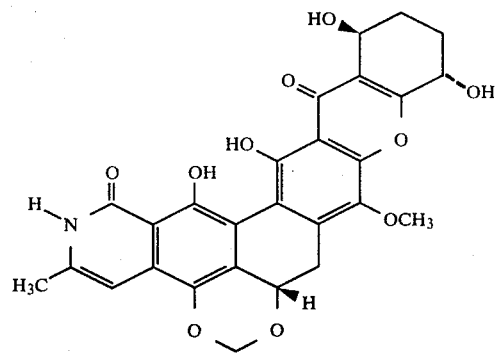

LL-D42067β

The physico-chemical characteristics of LL-D42067β are described below:
(1) Molecular weight: 521 (FAB-MS)
(2) Molecular formula: $C_{27}H_{23}NO_{10}$
(3) Specific optical rotation: $[\alpha]_D^{26} = +770 \pm 10°$ (C 0.165, DMF);
(4) Ultraviolet absorption spectra: as shown in FIG. I

| | | |
|---|---|---|
| $UV_{MAX}^{CH_3OH} =$ | 212 nm | (ε28,200) |
| | 253 nm | (ε33,200) |
| | 318 nm | (ε13,200) |
| | 378 nm | (ε19,700) |
| | 393 nm | (ε21,700) |
| $UV_{MAX}^{0.1\,N\,HCl} =$ | 211 nm | (ε13,900) |
| | 253 nm | (ε18,200) |
| | 318 nm | (ε7,140) |
| | 372 nm | (ε9,950) |
| | 388 nm | (ε10,500) |
| $UV_{MAX}^{0.1\,N\,NaOH} =$ | 216 nm | (ε31,200) |
| | 251 nm | (ε11,700) |

(5) Infrared absorption spectrum: as shown in FIG. II (KBr disc): 3400, 1646, 1620, 1545, 1463, 1252, 1195, 1020 cm$^{-1}$;
(6) Proton nuclear magnetic resonance spectrum (CDCl₃) as shown in FIG. III, and described in Table I;
(7) Carbon-13 nuclear magnetic resonance spectrum (CD₃OD/CDCl₃): as shown in FIG. IV and described in Table II.

TABLE I

| Proton NMR Data for LL-D42067β | | | |
|---|---|---|---|
| δ* | No. of Hydrogen | Multiplicity** | J (H) |
| 1.88 | 2 | m | |
| 2.30 | 2 | m | |
| 2.38 | 3 | s | |
| 2.57 | 2 | m | |
| 3.69 | 1 | d,d | 4.5, 14.3 |
| 3.87 | 3 | s | |
| 4.79 | 1 | m | |
| 4.81 | 1 | d,d | 4.5, 12.7 |
| 5.06 | 1 | m | |
| 5.32 | 1 | d | 5.8 |
| 5.53 | 1 | d | 5.8 |
| 6.54 | 1 | s | |
| 10.1 | 1 | s | |
| 12.8 | 1 | s | |
| 12.9 | 1 | s | |

*CDCl₃, ppm downfield from TMS.
**s = singlet;
d = doublet;
m = multiplet.

TABLE II

Carbon-13 NMR Data for LL-D42067β

| Carbon | Chemical Shift (ppm)* |
|---|---|
| 1 | 19.1 |
| 2 | 25.9 |
| 3 | 26.9 |
| 4 | 29.7 |
| 5 | 62.0 |
| 6 | 62.2 |
| 7 | 65.0 |
| 8 | 72.8 |
| 9 | 91.1 |
| 10 | 100.1 |
| 11 | 110.5 |
| 12 | 110.6 |
| 13 | 111.7 |
| 14 | 114.7 |
| 15 | 119.2 |
| 16 | 127.2 |
| 17 | 128.8 |
| 18 | 136.1 |
| 19 | 136.3 |
| 20 | 137.0 |
| 21 | 138.1 |
| 22 | 148.9 |
| 23 | 151.9 |
| 24 | 153.0 |
| 25 | 165.3 |
| 26 | 167.2 |
| 27 | 183.6 |

*$CD_3OD/CDCl_3$, ppm downfield from TMS.

The protozoacidally-effective compound of this invention, designated LL-D42067β, is formed during the cultivation under controlled conditions of a new strain of a new subspecies of *Actinomadura madurae*. This new strain is maintained in the culture collection of the Medical Research Division, American Cyanamid Company, Pearl River, N.Y. as culture number LL-D42067β. A viable culture of this new microorganism has been deposited with the Patent Culture Collection Laboratory, Northern Regional Research Center, U.S. Department of Agriculture, Peoria, Ill. 61604, and has been added to its permanent collection. It is freely available to the public in this depository under its accession number NRRL 15734.

Culture LL-D42067β was isolated from a soil sample from San Simao, Brazil. The culture was taxonomically characterized and was identified as a new subspecies of *Actinomadura madurae*, designated *Actinomadura madurae* subspecies simaoensis.

Observations were made of the cultural, physiological and morphological features of the culture in accordance with the methods detailed by Shirling and Gottlieb [Intern. J. System. Bacteriol. 16:313–340 (1966)] and Gordon, et al. [Intern. J. System. Bacteriol., 24:54–63 (1974)]. The chemical composition of the cell walls of the culture was determined using the method of Lechevalier, et al. [Adv. Appl. Microbiol. 14:47–72 (1971)]. Details are recorded in Tables III–V, and a general description of the culture is given below. Underscored descriptive colors are taken from Kelly and Judd [Nat. Bur. Stand., Spec. Publ., 440 (1976)] and the accompanying Intersociety Color Council, National Bureau of Standards Centroid Color Charts.

Growth Characteristics

Table III describes the cultural characteristics of culture LL-D42067β on various agar media which were selected from those recommended by the International Streptomyces Project Committee (hereinafter referred to as "ISP").

Micromorphology

Microscopic examination of the strain showed it to form short chains of conidia on aerial hyphae which were slightly hooked to short-spirals (up to three turns). The spore surfaces were smooth when observed by electron microscopy, distinguishing this isolate from *A. verrucosopora*.

Cell Wall Composition

Whole cell analyses showed the strain to contain meso diaminopimelic acid (DAP) and the sugar 3-O-methyl-D-galactose (madurose); thus it falls into whole cell pattern type B. The cell wall composition was of the type III (meso DAP, glutamic acid, alanine, muramic acid and glucosamine) and the phospholipid pattern of type PIV (phosphatidyl ethanolamine and/or methylethanolamine plus unknown glucosamine-containing phospholipids). These data support the assignment of the strain to the genus Actinomadura. The PIV phospholipid type is not typical for *A. madurae*, which is usually PI.

Physiological Reactions

The physiological reactions of strain LL-D42067 were examined using both the ISP system, Shirling and Gottlieb [Intern. J. Syst. Bacteriol., 16:313–340 (1966)] and the Gordon tests, Gordon, et al. [Intern. J. Syst. Bacteriol., 24:54–63 (1974)]. The utilization pattern of the strain on ISP carbohydrate media is given in Table IV, along with those of other members of the genus reacting similarly. Culture LL-D42067 resembles the *Actinomadura madurae* and *Actinomadura verrucosopora* groups. As indicated above, however, it differs from *Actinomadura verrucosopora* in having smooth spore walls. A comparison of reactions in the Gordon test series of *Actinomadura madurae* (Gordon's data; see reference above) and LL-D42067, summarized in Table V, revealed differences only in amylase production and acid from glycerol and raffinose. Since amylase production and raffinose utilization have been found to be variable in *Actinomadura madurae* [Goodfellow, N., et al., J. Gen. Microbiol., 112:95–111 (1979)], the glycerol reaction remains the only physiological difference of LL-D42067 from this taxon.

Since strain LL-D42067 is the same as *Actinomadura madurae* in all properties evaluated except for its glycerol reaction and its PIV phospholipid pattern, it has been assigned to the taxon *Actinomadura madurae* as a subspecies designated *Actinomadura madurae* subspecies simaoensis.

TABLE III

Cultural Characteristics of LL-D42067 *Actinomadura madurae* subspecies simaoensis on ISP Morphological Media

| Agar Medium | Aerial Mycelium | Vegetative Mycelium | Soluble Pigment |
|---|---|---|---|
| Yeast extract, Malt extract (ISP 2) | White, sparse | Medium orange-brown-I53* | None |
| Inorganic Salts Starch (ISP 4) | Colorless | Colorless | None |
| Glucose Asparagine (ISP 5) | Colorless | Colorless | None |
| Oatmeal (ISP 3) | Sparse pinkish-white | Light orange-brown-I52* | None |

*I = ISCC Color charts

TABLE IV

Comparison of Carbohydrate Utilization Reactions of LL-D42067 With Related Actinomadura spp.

| Carbohydrate | LL-D42067 | A. madurae (a) | A. verrucosopora (a) (b) |
|---|---|---|---|
| L-arabinose | + | + | + |
| D-fructose | + | + | + |
| I-inositol | − | variable | variable |
| D-mannitol | + | + | + |
| raffinose | − | − | − |
| rhamnose | + | + | + |
| sucrose | + | + | + |
| D-xylose | + | + | + |

(a) Goodfellow, M., et al., J. Gen. Microbiol., 112:95-111 (1979).
(b) Nonomura, H. and O'Hara, Y., J. Ferm. Technol., 49:904-912 (1971).

TABLE V

Gordon Test Reactions of LL-D42067

| | LL-D42067 | A. madurae (Gordon Data*) |
|---|---|---|
| Degradation/Transformation of | | |
| Casein | + | +(98) |
| Xanthine | − | − |
| Hypoxanthine | + | +(98) |
| Tyrosine | + | +(91) |
| Adenine | − | − |
| Production of | | |
| Amylase | − | + |
| Gelatinase | + | + |
| Phosphatase | − | ND |
| Nitrate Reductase | + | +(98) |
| Urease | − | − |
| Esculinase | + | +(98) |
| Growth on/in | | |
| 5% Sodium Chloride | − | ND |
| Salicylate | − | ND |
| Lysozyme Broth | − | −(91) |
| Utilization | | |
| Acetate | + | + |
| Benzoate | − | −(94) |
| Citrate | − | +(83) |
| Lactate | + | ND |
| Malate | + | +(84) |
| Mucate | − | − |
| Oxalate | − | ND |
| Propionate | − | ND |
| Pyruvate | + | ND |
| Succinate | + | +(83) |
| Tartrate | − | − |
| Growth at | | |
| 10° C. | − | − |
| 45° C. | + | −(66) |
| 53° C. | − | − |
| Acid from | | |
| Adonitol | + | +(91) |
| Arabinose | + | + |
| Cellobiose | + | + |
| Dextrin | + | ND |
| Dulcitol | − | − |
| Erythritol | − | − |
| Fructose | + | ND |
| Galactose | + | +(84) |
| Glucose | + | + |
| Glycerol | − | + |
| Inositol | − | +(60) |
| Lactose | − | +(55) |
| Maltose | − | +(53) |
| Mannitol | + | + |
| Mannose | + | +(94) |
| Melibiose | − | − |
| α-Methyl-D-glucoside | − | − |
| Raffinose | variable | − |
| Rhamnose | + | + |
| Salicin | + | ND |
| Sorbitol | − | − |
| Sucrose | + | ND |
| Trehalose | + | +(96) |
| Xylose | + | + |
| β-Methyl-D-xyloside | + | ND |

*Percentages of cultures showing reaction given in parentheses if not 100%.
ND = Not determined.

For the production of this new antibacterial and antiparasitic agent the present invention is not limited to this particular organism or to organisms fully answering the above growth and microscopic characteristics, which are given for illustrative purposes only. In fact, it is desired and intended to include the use of naturally-occurring mutants of this organism as well as induced mutants produced from this organism by various mutagenic means known to those skilled in the art such as exposure to nitrogen mustard, X-ray radiation, ultraviolet radiation, N'-methyl-N'-nitro-N-nitrosoguanidine, actinophages and the like. It is also desired and intended to include inter- and intraspecific genetic recombinants produced by genetic techniques known to those skilled in the art such as, for example, conjugation, transduction and genetic engineering techniques.

The in vitro antimicrobial spectrum of LL-D42067β was determined by the agar plate dilution method with Mueller-Hinton agar and an inoculum of each test organism of approximately $10^4$ colony forming units delivered by the Steers replicating device. The minimal inhibitory concentration (MIC) in mcg/ml was defined as the lowest concentration of LL-D42067β that inhibited visible growth after 18 hours incubation at 35° C.

The results, summarized in Table VI, show that LL-D42067β was active versus gram-positive bacteria and moderately active against yeasts.

TABLE VI

Antimicrobial Spectrum of LL-D42067β

| Test Organism | | MIC (mcg/ml) |
|---|---|---|
| Candida albicans | CA 300 | 512 |
| Saccharomyces cerevisiae | Y 15 | 512 |
| Mycobacterium smegmatis | ATCC 607 | 512 |
| Bacillus subtilis | ATCC 6633 | 4 |
| Bacillus cereus | LL No. 4 | ≦0.06 |
| Enterococcus | OSU 75-1 | 1 |
| Enterococcus | SM 77-15 | 2 |
| Streptococcus faecalis | ATCC 29212 | 1 |
| Streptococcus mutans | ATCC 27352-1 | 0.25 |
| Streptococcus mutans | BHI (b) | 0.25 |
| Streptococcus sanguis | G9B (a) | 0.5 |
| Staphylococcus epidermidis | CMC 83-56 | 0.5 |
| Staphylococcus epidermidis | ATCC 12228 | 0.25 |
| Staphylococcus aureus | Smith | 0.5 |
| Staphylococcus aureus | LL No. 14 | 0.5 |
| Staphylococcus aureus | LL No. 27 | ≦0.06 |
| Staphylococcus aureus | LL No. 45 | 0.12 |
| Staphylococcus aureus | ATCC 25923 | 0.25 |
| Micrococcus luteus | PC 1001 | ≦0.06 |
| Escherichia coli | No. 311 | 512 |
| Escherichia coli | ATCC 25922 | 512 |
| Acinetobacter calcoaceticus | STFD 79-17 | 512 |

The antibiotic LL-D42067β derives utility from its antibacterial and antiparasitic activities. For example, the antibiotic may be used in the suppression of intestinal bacterial flora, as a topical antibacterial agent or antiseptic against gram-positive bacteria and as a general disinfectant for surfaces such as instruments. It may also be useful as an antiprotozoal agent in the treatment of malaria. In addition to its antimicrobial and antiparasitic activity LL-D42067β is effective as an anticoccidial agent in poultry. This utility is the subject of a copending application for U.S. letters patent.

In therapeutic use, the compound of this invention may be administered in the form of conventional pharmaceutical compositions appropriate for the intended use. Such compositions may be formulated so as to be suitable for oral or topical administration. The active ingredient may be combined in admixture with a nontoxic pharmaceutically acceptable carrier, which carrier may take a wide variety of forms depending on the form of preparation desired for administration, i.e., oral or topical.

General Fermentation Conditions

Cultivation of *Actinomadura madurae* subspecies simaoensis NRRL 15734 may be carried out in a wide variety of liquid culture media. Media which are useful for the production of this novel antibiotic LL-D42067β include an assimilable source of carbon, such as dextrin, sucrose, molasses, glycerol, etc.; an assimilable source of nitrogen such as protein, protein hydrolysate, polypeptides, amino acids, corn steep liquor, etc.; and inorganic anions and cations, such as potassium, sodium, ammonium, calcium, sulfate, carbonate, phosphate, chloride, etc. Trace elements such as boron, molybdenum, copper, etc., are supplied as impurities of other constituents of the media. Aeration in tanks and bottles is supplied by forcing sterile air through or onto the surface of the fermenting medium. Further agitation in tanks is provided by a mechanical impeller. An antifoam agent such as silicone oil may be added as needed.

General Procedure for the Isolation of LL-D42067β

Antibiotic LL-D42067β is recovered from the whole harvest mash by filtration through a medium such as diatomaceous earth, extraction into a solvent such as ethyl acetate, concentration to a syrup, partitioning between heptane and methanol and concentration of the methanol phase to a residue. This residue is triturated with hexane, then concentrated to a residue which is dissolved in a mixture of equal parts acetonitrile and water and then evaporated giving a precipitate. This precipitate is purified by preparative reverse phase high performance liquid chromatography (HPLC) using the system acetonitrile:water:acetic acid (3000:6000:5). The active fractions are combined, evaporated to an aqueous suspension and extracted with ethyl acetate which is evaporated to obtain the pure LL-D42067β.

EXAMPLE 1

Inoculum Preparation

A typical medium used to grow the various stages of inoculum was prepared according to the following formula:

| Dextrose | 1.0% |
|---|---|
| Dextrin | 2.0% |
| Yeast extract | 0.5% |
| NZ Amine A ®' | 0.5% |
| Calcium carbonate | 0.1% |
| Water qs | 100% |

NZ Amine A ®' (A pancreatic digest of casin; registered trademark of Sheffield Chemical, Norwich, New York)

This medium was sterilized. A 100 ml portion of this sterile medium, in a flask, was inoculated with mycelial scrapings from an agar slant of *Actinomadura madurae* subspecies simaoensis NRRL 15734. The medium was then agitated vigorously on a rotary shaker for 48–72 hours at 28° C. providing primary inoculum. This primary inoculum was then used to inoculate 10 liters of the above sterile medium, which was then grown at 28° C. for 48 hours, providing secondary inoculum. This secondary inoculum was then used to inoculate 250 liters of the above sterile medium, in a tank, which was grown for 48 hours at 28° C. with a flow of sterile air of 200 liters per minute, providing tertiary inoculum.

EXAMPLE 2

Fermentation

A fermentation medium of the following formulation was prepared.

| Sucrose | 3.0% |
|---|---|
| Soy flour | 1.5% |
| Corn steep liquor | 0.5% |
| Calcium carbonate | 0.5% |
| Water qs | 100% |

This medium was sterilized and then inoculated with 125 liters of tertiary inoculum, prepared as described in Example 1, per 3000 liters of the above sterile fermentation medium. The fermentation was conducted at 28° C. with a sterile air flow of 6.6 liters per liter of mash, agitation by an impeller operated at 110 rpm and the addition of silicone defoamer agent for 137 hours, at which time the mash was harvested.

EXAMPLE 3

Isolation of LL-D42067β

A total of 4500 liters of harvest mash combined from two fermentations conducted essentially as described in Example 2 was combined with 1% of its volume of diatomaceous earth, mixed for one hour and then the pH was adjusted to 3.0±0.3 with concentrated hydrochloric acid. One half the mash volume of ethyl acetate was added and this mixture was stirred for 3 hours. Diatomaceous earth equal to 5% of the mash volume was added and the mixture was filtered. The ethyl acetate phase of the filtrate was separated, washed with 5% aqueous sodium bicarbonate and then concentrated to a syrup. This material was partitioned between heptane:methanol (2:1).

The 4.5 liters of methanol phase was concentrated to a residue which was triturated with hexane. The hexane was decanted and the residue concentrated to dryness. This material was purified by preparative reverse phase HPCL with the following conditions: (A 300 g silica-based octa decyl(C)bonded phase packing material (deminsions 5.7 cm×30 cm), registered trademark of Wieley Associates, Inc., Milford, Mass.)

Column: A single PrepPAK ®-500/C$_{18}$ cartridge.
Mobile Phase
   1: Acetonitrile:water:acetic acid (8,000:12,000:10).
   2: Acetonitrile:water:acetic acid (3,000:6,000:5).
Flow Rate: 50 ml/minute.
Fractionation: 200 ml/fraction.
Sample Load: 2–3 per 30 ml injection.

Using mobile phase 1, LL-D42067β was found in fractions 7–10. These fractions were combined and evaporated in vacuo to remove the bulk of actonitrile. The resulting aqueous suspension was treated with an equal volume of ethyl acetate. The ethyl acetate phase was separated and sequentially washed with equal volumes of 5% aqueous sodium bicarbonate, 0.1N hydrochloric acid and twice with water. The organic phase was dried over anhydrous sodium sulfate and evaporated to a solid.

This solid was rechromatographed using mobile phase 2. In this mobile phase LL-D42067β was found in fractions 15-21 which were combined and treated as described above, giving pure LL-D42067β as a yellow solid.

EXAMPLE 4

Evaluation of Test Compounds as Anticoccidial Agents

The usefulnes of antibiotic LL-D42046β as an anticoccidial agent for chickens is demonstrated in the following tests.

The poultry diet employed in the test is as follows:

| | |
|---|---|
| Vitamin-amino acid premix | 0.5% |
| Trace minerals | 0.1% |
| Sodium chloride | 0.3% |
| Dicalcium phosphate | 1.2% |
| Ground limestone | 0.5% |
| Stabilized fat | 4.0% |
| Dehydrated alfalfa, 17% protein | 2.0% |
| Corn gluten meal, 41% protein | 5.0% |
| Menhaden fish meal, 60% protein | 5.0% |
| Soybean oil meal, 44% protein | 30.0% |
| Ground yellow corn, fine to | 100.0% |

The vitamin-amino acid premix in the above feed composition is prepared from the following formulation. The expressions of quantity relate to units per kilogram of the finished feed composition.

| | |
|---|---|
| Butylated hydroxy toluene | 125.0 mg |
| dl-Methionine | 500.0 mg |
| Vitamin A | 3300.0 I.U. |
| Vitamin $D_3$ | 1100.0 I.C.U. |
| Riboflavin | 4.4 mg |
| Vitamin E | 2.2 I.U. |
| Niacin | 27.5 mg |
| Panthothenic acid | 8.8 mg |
| Choline chloride | 500.0 mg |
| Folic acid | 1.43 mg |
| Menadione sodium bisulfate | 1.1 mg |
| Vitamin $B_{12}$ | 11.0 mcg |
| Ground yellow corn, fine to | 5.0 gm |

A mixed inoculum of 5000 sporulated oocysts of *Eimeria acervulina* and a sufficient number of oocysts of *Eimeria tenella* to produce 60% to 75% mortality in untreated controls were given to one-day-old chicks, by direct inoculation into the crops of all chicks. The chicks were given free access to feed and water during the entire test period. Two days before inoculation, medicated feed with several levels of drug was presented to the various groups of chicks. Seven days after inoculation, the tests were terminated and the chicks were weighed, necropsied, and their intestinal tracts examined for lesions. The results appear in the Table below. These results show that improved survival of infected chicks is obtained when 0.5 ppm to 5.0 ppm of the antibiotic is administered to infected chicks in their diet. These levels also show a significant suppression of lesions due to *E. tenella* and *E. acervulina*.

TABLE VI

EVALUATION OF ANTIBIOTIC LL-D42067β AS AN ANTICOCCIDIAL AGENT IN CHICKS

| Compound | Concentration in Diet, ppm | No. Chicks Started | Percent Survival | Percent Chicks with Reduced Lesions *E. tenella* |
|---|---|---|---|---|
| LL-D42046β | 5.0 | 5 | 80 | 100 |
| LL-D42067β | 2.5 | 5 | 100 | 100 |
| LL-D42067β | 1.00 | 5 | 80 | 80 |
| LL-D42067β | 0.75 | 5 | 60 | 40 |
| LL-D42067β | 0.5 | 5 | 40 | 0 |
| Infected Untreated Control | 0.0 | 20 | 35 | 0 |

What is claimed is:

1. A method for the control of protozoan infections in warm-blooded animals, said method comprising: administering to the animals a protozoacidally-effective amount of a compound of the formula,

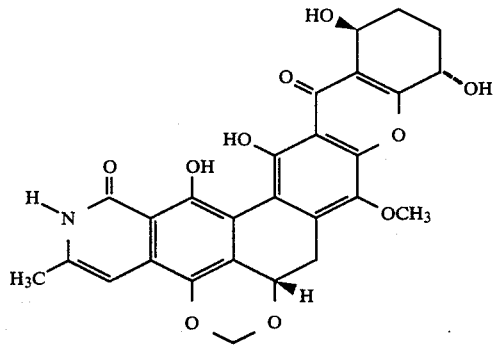

LL-D42067β or a pharmaceutically and pharmacologically acceptable salt thereof.

2. A method according to claim 1, wherein the warm-blooded animals are meat-producing animals, the protozoan infection is coccidiosis, and the anticoccidial agent has the formula,

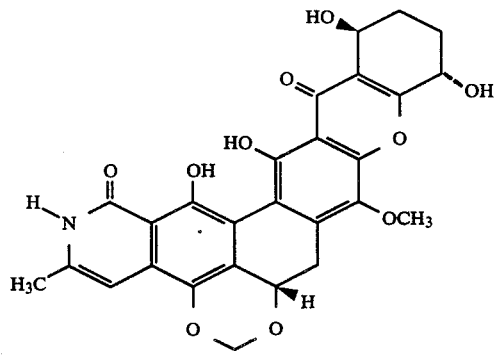

LL-D42067β or a pharmaceutically and pharmacologically acceptable salt thereof; and the anticoccidial agent is orally administered to the meat-producing animals in a solid or liquid carrier containing 0.1 ppm to 100 ppm of the anticoccidial agent.

3. A method according to claim 1, wherein the warm-blooded animals are meat-producing animals, the protozoan infection is coccidiosis, and the anticoccidial agent has the formula,

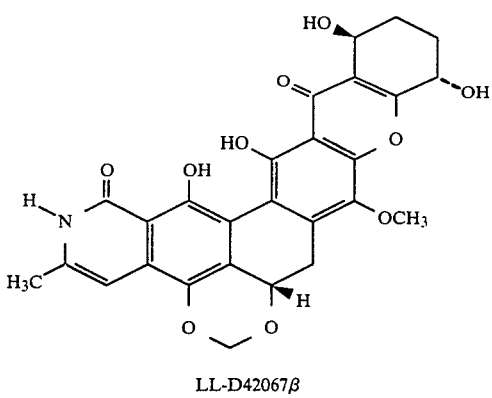

LL-D42067β or a pharmaceutically and pharmacologically acceptable salt thereof; and the anticoccidial agent is parenterally administered to the animals in a solid or liquid carrier containing 0.1 ppm to 100 ppm of the anticoccidial agent.

4. A method according to claim 1, wherein the protozoacidally-effective compound is administered to the animal in a dose range of from 0.003 mg/kg of body weight/day to about 3.0 mg/kg of body weight/day.

5. A method according to claim 2, wherein the animals are poultry; and the anticoccidial agent is administered thereto in feed or drinking water containing 0.1 ppm to 10.0 ppm of the anticoccidial agent.

6. A method according to claim 2, wherein the animals are cattle, sheep, or swine; and the anticoccidial agent is administered thereto in feed or drinking water containing 1.0 ppm to 100 ppm of the anticoccidial agent.

7. An animal feed or animal feed premix composition for the control of coccidiosis infections in meat-producing animals, said animal feed or animal feed premix comprising: a solid edible carrier; and about 0.00001% by weight to about 5.0% by weight of a compound of the formula,

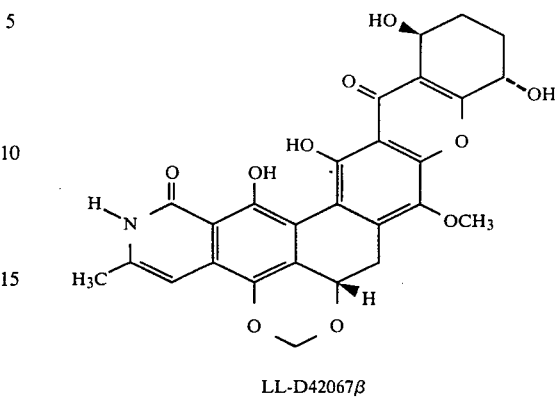

LL-D42067β or a pharmaceutically and pharmacologically acceptable salt thereof.

8. An animal feed or animal feed premix composition according to claim 7, wherein said animals are poultry; and said composition comprises: about 0.00001% by weight to about 0.001% by weight of a compound of the formula,

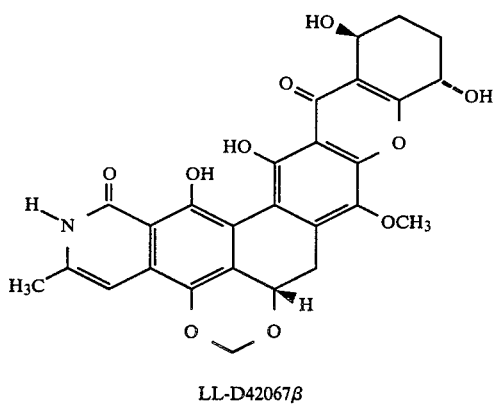

LL-D42067β or a pharmaceutically and pharmacologically acceptable salt thereof.

* * * * *